(12) United States Patent
Gragg et al.

(10) Patent No.: US 7,822,623 B2
(45) Date of Patent: Oct. 26, 2010

(54) SYSTEM AND METHOD FOR COST ACCOUNTING IN A HEALTHCARE ENVIRONMENT

(75) Inventors: John H. Gragg, Overland Park, KS (US); Brian J. Lancaster, Merriam, KS (US); Kent D. Parkins, Parkville, MO (US); Michael E. Yarbrough, Lees Summit, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1330 days.

(21) Appl. No.: 11/022,654

(22) Filed: Dec. 28, 2004

(65) Prior Publication Data

US 2006/0143042 A1    Jun. 29, 2006

(51) Int. Cl.
*G06Q 10/00* (2006.01)
*G06Q 50/00* (2006.01)

(52) U.S. Cl. .................. 705/2; 705/3; 705/4; 705/8; 705/40

(58) Field of Classification Search ............... 705/2–4, 705/8, 40
See application file for complete search history.

(56) References Cited

U.S. PATENT DOCUMENTS

| | | | |
|---|---|---|---|
| 4,667,292 A * | 5/1987 | Mohlenbrock et al. | 705/2 |
| 5,732,401 A | 3/1998 | Conway | |
| 7,149,700 B1 * | 12/2006 | Munoz et al. | 705/8 |
| 2004/0002924 A1 * | 1/2004 | Boone et al. | 705/400 |
| 2005/0038670 A1 * | 2/2005 | Takkar et al. | 705/2 |
| 2008/0052124 A1 * | 2/2008 | Goodman et al. | 705/3 |

OTHER PUBLICATIONS

Final Office Action mailed Oct. 26, 2009 re U.S. Appl. No. 11/325,019, filed Jan. 3, 2006.
Non-Final Office Action mailed Feb. 5, 2009 re U.S. Appl. No. 11/325,019, filed Jan. 3, 2006.
Non-Final Office Action mailed Apr. 27, 2010 re U.S. Appl. No. 11/325,019, filed Jan. 3, 2006.

* cited by examiner

*Primary Examiner*—Gerald J. O'Connor
*Assistant Examiner*—Linh-Giang Michelle Le
(74) *Attorney, Agent, or Firm*—Shook, Hardy & Bacon L.L.P.

(57) ABSTRACT

The present invention is directed to a method and system for generating cost accounting data. The method may include retrieving information including descriptive attributes that represent content captured during patient care. The method may additionally include associating each descriptive attribute with a cost. A system may be provided for generating cost accounting information in a healthcare environment. The system may include automated information capture equipment and a retrieval component for retrieving content captured by the automated information capture equipment. The system may additionally include an association component for associating captured content with a cost and an implementation component for generating cost accounting information based on created associations.

21 Claims, 3 Drawing Sheets

SYSTEM AND METHOD FOR COST ACCOUNTING IN A HEALTHCARE ENVIRONMENT

CROSS-REFERENCE TO RELATED APPLICATIONS

None.

STATEMENT REGARDING FEDERALLY SPONSORED RESEARCH OR DEVELOPMENT

None.

TECHNICAL FIELD

Embodiments of the present invention relate to techniques for cost accounting. More particularly, embodiments of the invention are directed to techniques for cost accounting in a healthcare environment.

BACKGROUND OF THE INVENTION

Cost accounting is the general practice of taking costs or expenses that are recorded on a general ledger system and allocating the costs and expenses to volumes of provided goods and services. In a general ledger system, costs and expenses are recorded by the department or area in which they are incurred. Since products and services provided are typically supported by multiple departments or areas, the costs recorded on the general ledger for any particular department will therefore only represent a portion of the total costs for any particular product or service. This phenomenon is particularly true in healthcare, as a patient will likely receive services from many different departments during the patient's treatment.

In its first generation form, cost accounting in healthcare was introduced through its use as a government reimbursement methodology for Medicare. Given the government's commitment to reimburse healthcare providers based on their costs, a system was required to calculate the costs associated with the provision of services to Medicare patients.

The "Ratio of Cost to Charges" technique arose in response to the Medicare system. The technique allocated costs based on the portion of total charges for a particular department that were produced by Medicare patients. The higher that Medicare charges were as a percentage of total charges for a particular department, the higher the costs that would be allocated to Medicare patients, and hence reimbursed by the government. The ratio of cost to charge approach assumed that charges were a close approximation to the level of resources actually incurred in the provision of any chargeable service. At the time the approach was introduced, this was generally the case, as most providers established charge rates as a mark-up from costs of individual goods and services.

Over time, hospitals learned that by increasing the charge amounts for procedures that had a heavy utilization by Medicare patients, their reimbursement by the government could be increased. This process was known as cost-shifting, and became prevalent throughout the industry. The relative relationship between the costs and their associated charges for goods and services became distorted. Charges for services that were utilized heavily by Medicare patients were artificially inflated. In many facilities, the ratio of cost to charge approach resulted in inaccurate cost estimates such that charges no longer could be used as an estimate of resources utilized in providing any particular service.

Further cost accounting techniques arose as a response to payment methodologies later introduced by the government. The government changed reimbursement formulas from cost-based to a preset amount based on the diagnosis of the patient. Thus, cost accounting methodologies developed that focused on breaking down the provision of patient care into procedures. The procedure costs could subsequently be combined into the total costs for every patient based on the procedures used for each particular case or stay.

In response, many facilities initially developed a "bill of materials" for each chargeable procedure, which equated to a direct cost that could be identified based on the labor, supplies, and other materials used in that procedure. The method then calculated the difference between the summation of these individual costs and the costs reported on the general ledger, and allocated this difference using the direct costs as an allocation basis. This allocation procedure, generally called "Standards Development", was derived from the management accounting practices used in the manufacturing industry.

For some institutions, the standards development approach was too costly to maintain due to the dynamic nature of how patients are treated in the healthcare setting. Based on individual physician preferences, changes in technology, and differences between costs of supplies and pharmaceuticals between various vendors, the list of resources used in the provision of services for any particular procedure could change monthly and even weekly. Most facilities that did not have a dedicated staff of management engineers ended up abandoning this methodology.

Subsequently, an approach called Relative Value Units (RVUs), evolved for allocation of general ledger costs to the individual procedures performed in a facility. Instead of building a bill of materials for each procedure, this approach uses a single statistic, or RVU, as the basis for allocation of general ledger costs to a chosen volume indicator. While this approach does not specifically identify the direct costs associated with each charge item, as long as the "relative" relationship between each charge item was correct for a particular department, the end result of the allocation of general ledger costs was very close to the total costs that were calculated using the earlier standards development approach. Limitations of the above approach became apparent in the industry. Specifically, healthcare managers noticed that these costs represented the average cost and not the actual cost of providing any particular service.

Further refinements have led to a methodology known as "Activity Based Costing", which refines the unit indicators derived from charge items to actual activities identified in the provision of patient care. These activities, requiring manual capture, are then assigned a cost based on the amount of time required to perform the activity and the wage rate of the staff that performed the services. Effective use of this approach requires an investment to capture these activity volumes.

Accordingly, a cost accounting solution is needed that overcomes the difficulties of the above approaches. Specifically, a cost accounting method is needed that provides for automated association and accumulation of volumes. Furthermore, a solution is needed that eliminates distorted results and improves accuracy of cost accounting results.

BRIEF SUMMARY OF THE INVENTION

In accordance with an embodiment of the invention, a method is provided for generating cost accounting information in a healthcare environment. The method includes retrieving information including descriptive attributes, wherein the descriptive attributes represent content electronically captured during patient care. The method may additionally include associating each descriptive attribute with a cost. Embodiments of the method may further include combining the cost of each descriptive attribute classified in a category in order to determine a category cost.

In an additional embodiment, a system is provided for generating cost accounting information in a healthcare environment including automated information capture equipment. The system includes a retrieval component for retrieving content captured by the automated information capture equipment. The system may additionally include an association component for associating captured content with a cost. The system may also include an implementation component for generating cost accounting information based on created associations.

BRIEF DESCRIPTION OF THE DRAWINGS

The present invention is described in detail below with reference to the attached drawings figures, wherein.

DETAILED DESCRIPTION OF THE INVENTION

Embodiments of the present invention are directed to a system and method for managing cost accounting in an accurate and automated manner. The approach described herein includes the allocation of costs to a clinical attribute or event. More specifically, the approach involves the relative application of descriptive attributes and events as volume indicators for the cost allocation process in a healthcare environment.

The method and system for managing cost accounting using descriptive attributes allows for automated association and accumulation of volumes, thus providing for simplified maintenance and generation of cost accounting results. Descriptive attributes, which will be further defined below, provide an increased level of granularity to contribute to the improved accuracy of cost accounting results.

Figure 1:
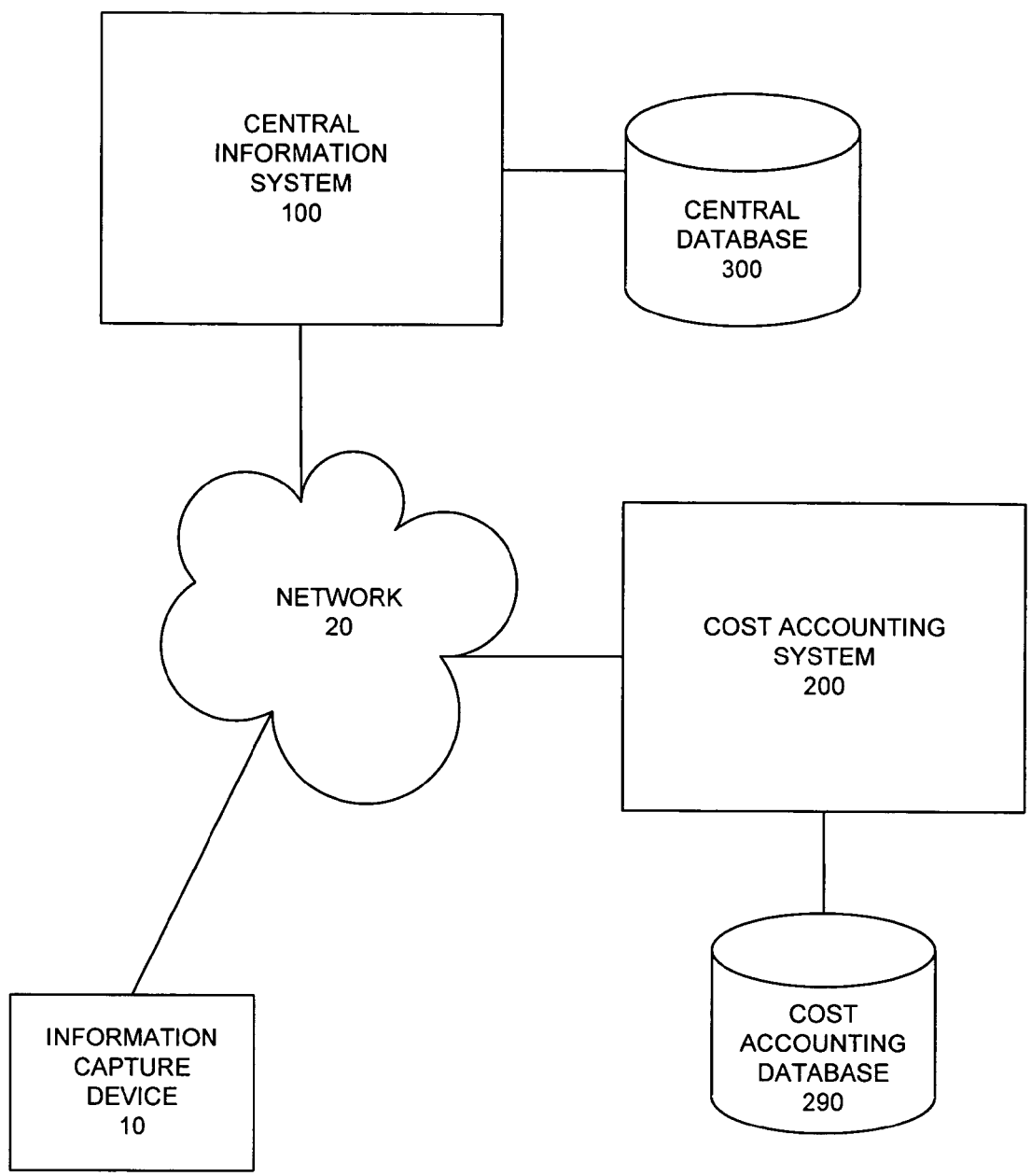
FIG. 1 is a block diagram illustrating components of a system for managing cost accounting in accordance with an embodiment of the invention.

The following discussion describes embodiments of the invention with reference to FIGS. 1-4. FIG. 1 illustrates an environment in which cost accounting may be managed. An information capture device 10 may be connected over a network 20 with a central information system 100. The central information system 100 may be connected with a central database 300. A cost accounting system 200 may also be connected over the network 20 and may optionally access a cost accounting database 290. Alternatively, the cost accounting database 290 may be excluded and all relevant information may be stored in the central database 300.

The information capture device 10 may capture content of a fine level of granularity and each piece of captured content can be defined as a clinical attribute. In a clinical setting, a patient may be viewed as the broadest category. To reach lower levels of granularity, an encounter with a patient is considered. The encounter leads to a physician procedure or order, followed by a resultant events and activities. These events and activities are captured by the information capture device 10.

The information capture device 10 may be or include a caregiver portable computing device that enables a caregiver to record each event that occurs with respect to a patient. The information capture device 10 may be a personal computer, and typically includes many of the elements described below relative to the central information system 100. In embodiments of the invention, the information capture device 10 may include a memory, processing unit, battery, user interface tools, a network interface, RF communication tools, and identifier recognition tools. The identifier recognition tools may include a scanning device or other reading mechanism for reading machine-readable identifiers. The information capture device 10 may read machine-readable identifiers associated with a patient, a medication, or a piece of equipment to record the use of a medication or equipment and the treatment of a specific patient. After capture, the information capture device 10 may send the information over the network 20 to the central information system 100.

In order to implement the information capture device 10, each patient may be identified by a patient identification device and each medical device or medication may be identified by a medical device or medication identification device. A caregiver identification device may identify a caregiver. Upon transfer of identity information to the central information system 100, each caregiver, patient, and each medication or medical device can be verified with the central information system 100.

Furthermore, the information capture device 10 may include one or more devices that have the capability to capture such information as labor times in pathology tests, actual pharmaceutical costs and dispensing modes, supply chain acquisition costs, and radiology exam times. As will be explained below, this captured information is usable in the allocation of costs.

The central information system 100 preferably includes known computing components such as a memory, a processing unit, and interfaces for allowing communication with a user, a network, and peripheral devices. A system bus may couple the aforementioned components. Upon receiving captured information, the central information system 100 may store the information in the central database 300.

The memory of the central information system 100 may include computer storage media in the form of volatile and/or nonvolatile memory such as read only memory (ROM) and random access memory (RAM). A basic input/output system (BIOS), containing the basic routines that help to transfer information between elements within the central information system 100, such as during start-up, is typically stored in the ROM. The RAM typically contains data and/or program modules that are immediately accessible to and/or presently being operated on by processing unit. The central information system 100 may also include other removable/non-removable, volatile/nonvolatile computer storage media. A hard disk drive may be provided that reads from or writes to non-removable, nonvolatile magnetic media, a magnetic disk drive that reads from or writes to a removable, nonvolatile magnetic disk, and an optical disk drive that reads from or writes to a removable, nonvolatile optical disk such as a CD ROM or other optical media. Other removable/non-removable, volatile/nonvolatile computer storage media may be used.

By way of example, and not limitation, the central information system 100 may include an operating system, application programs, other program modules, and program data.

The application programs and other programs may be described in the general context of computer-executable instructions, such as program modules, being executed by a computer. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like.

A user may enter commands and information into the central information system 100 through a user interface using input devices such as a keyboard and pointing device, commonly referred to as a mouse, trackball or touch pad. Other input devices may also be used and may be connected to the processing unit through a user input interface that is coupled to a system bus or other structure.

The central information system 100 may operate in a networked environment in conjunction with the network 20 as illustrated in FIG. 1, using logical connections to one or more remote computers, such as the information capture device 10. The network 20 may be the Internet and all components of the system may be accessible over the Internet. Logical connections for networking may include a local area network (LAN) or a wide area network (WAN), but may also include other networks. When used in a LAN networking environment, the central information system 100 may be connected to the LAN through a network interface or adapter. When used in a WAN networking environment, the central information system 100 typically includes a modem or other means for establishing communications, such as the Internet.

Figure 3:
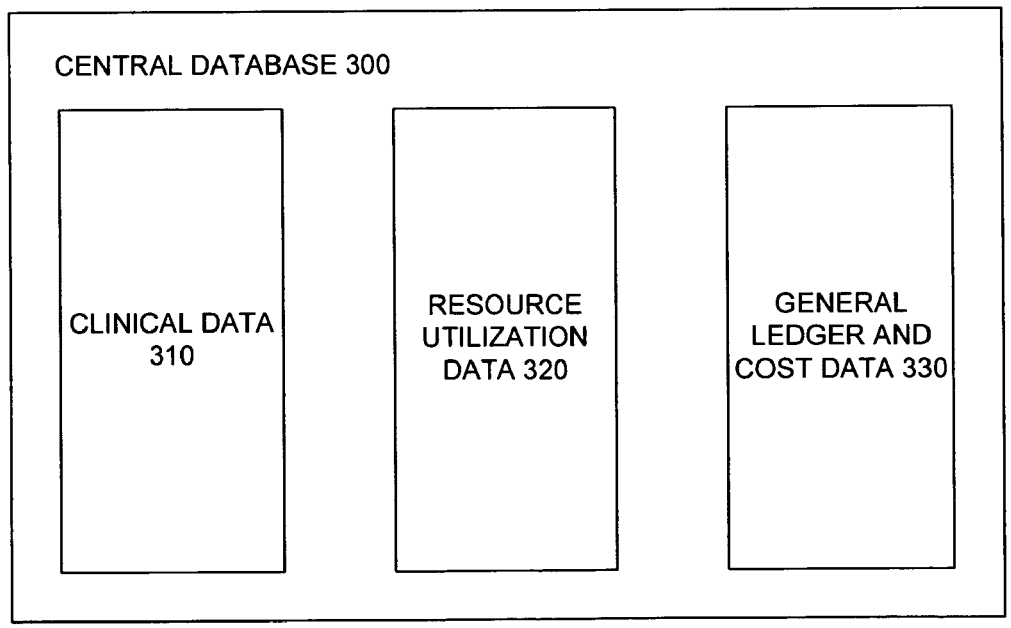
FIG. 3 is a block diagram illustrating components of a central database in accordance with an embodiment of the invention.

FIG. 3 illustrates the central database 300 in accordance with embodiments of the invention. The central database 300 may include clinical data 310, resource utilization data 320, and general ledger and cost data 330. The clinical data 310 may include a treatment history or an electronic health record (EHR) for each patient including orders entered by a physician for treatment of each patient. The clinical data 310 may also include information device settings and capabilities as well as each discrete usage of each device recorded by the information capture device 10. The clinical data 310 may also include records of assigned tasks for each caregiver in the system as well as each task performed by a caregiver as recorded by the information capture device 10.

Figure 2:
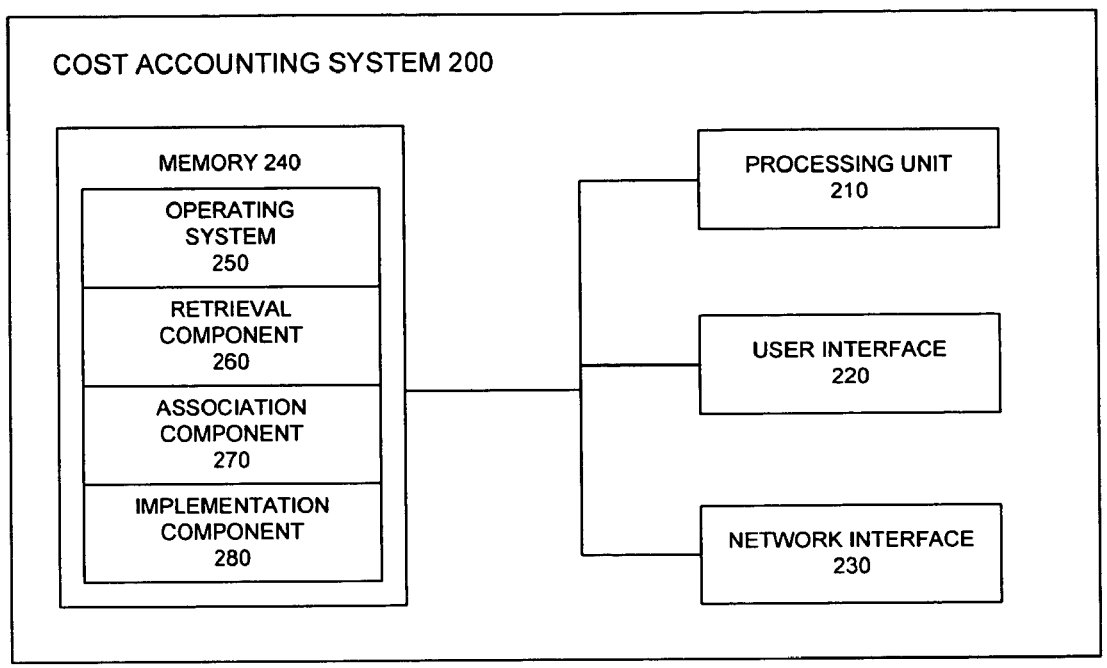
FIG. 2 is a block diagram illustrating components of a cost accounting system in accordance with an embodiment of the invention.

FIG. 2 illustrates further details of the cost accounting system 200 in accordance with an embodiment of the invention. The cost accounting system 200 may include a processing unit 210, a user interface 220 and a network interface 230. The cost accounting system 200 may additionally include a memory 240. The cost accounting system 200 may also include computing components such as those described above with reference to the central information system 100. The memory 240 may include an operating system 250, a retrieval component 260, an association component 270, and an implementation component 280. Optionally, the cost accounting system 200 may be connected with a cost accounting database 290. Alternatively, all data relevant to the cost accounting system 200, such as the general ledger and cost data 330, may be stored in the central information database 300.

The association component 270 may include cost algorithms for calculating costs at a selected level of granularity that is broader than the level of content captured and retrieved by the retrieval component 260. For instance, the association component 270 may determine all descriptive attribute costs and combine the descriptive attributes for a selected patient. Thus, the retrieval component 260 may retrieve information from the general ledger information 330 and captured content from the information capture device 10. The association component 270 may include algorithms for assigning costs to descriptive attributes or captured content. Many pieces of captured content can be associated with a selected patient and combined to allocate all costs for all content associated with the patient to the selected patient. The association component 270 may develop costs at the clinical event level, the charge level, the activity level, the clinical encounter level, or other selected level.

The implementation component 280 may include cost algorithms to further roll up costs by population. For instance, the implementation component 280 may roll up costs by product lines, services, physician, payer, or programs. Furthermore, the implementation component 280 can produce summarized cost information along virtually any dimension of the patient population. The implementation component 280 may produce cost analyses by physician, surgeon, procedure, and case. The implementation component 280 may also be configured to produce cost analyses by service line, diagnoses, program, department, financial class, payer, insurance plan, and contract. The operation of the retrieval component 260, the association component 270, and the implementation component 280 will be further described below in conjunction with an embodiment of the method for cost accounting.

The cost accounting system 200 may reside on a server platform, such as for example, a dedicated MS Windows or UNIX server platform running for example either SQL server 2000 or Oracle. Additional servers may also be included to support scalability and redundancy.

Figure 4:
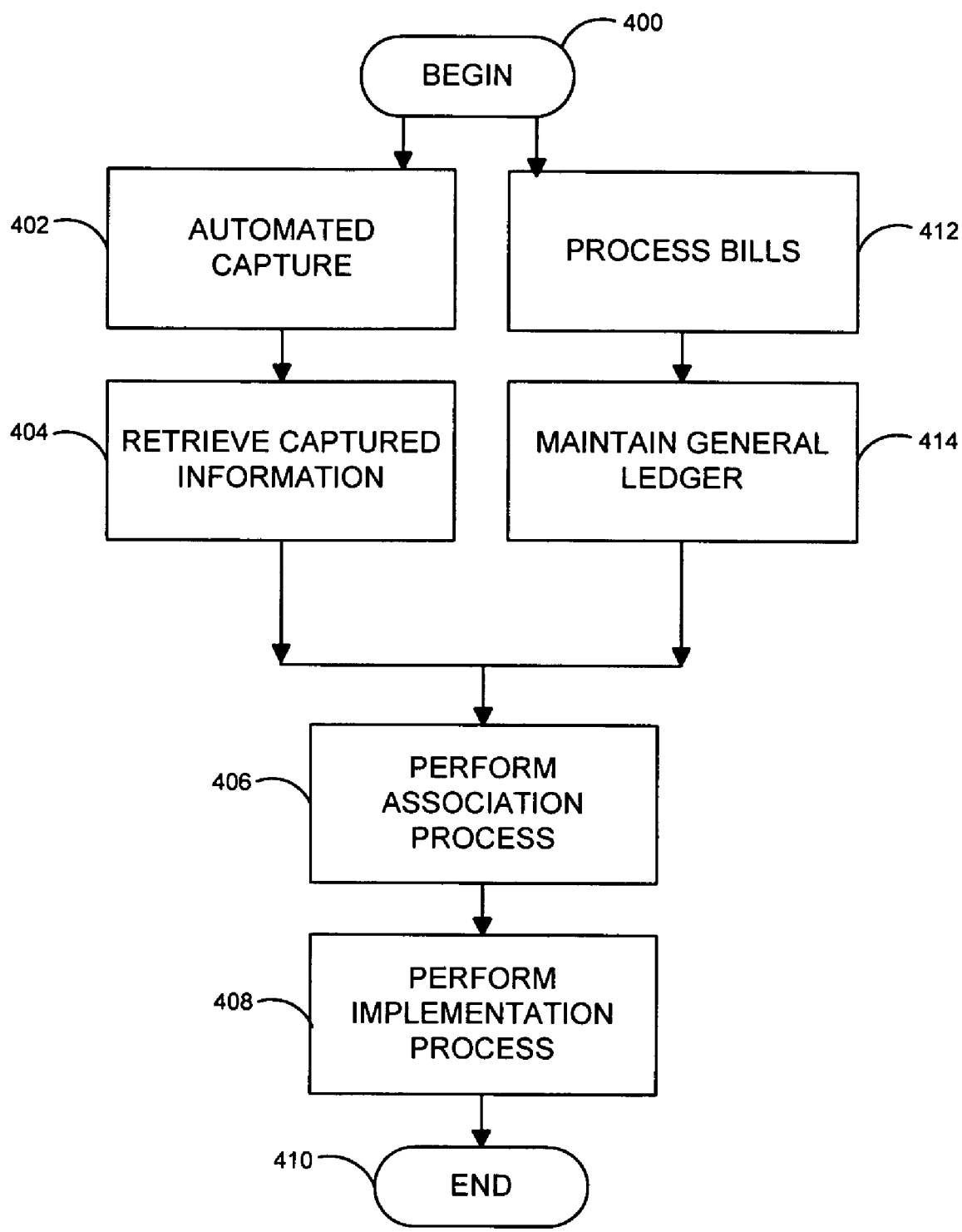
FIG. 4 is a block diagram illustrating a method for managing cost accounting in accordance with an embodiment of the invention.

To illustrate the operation of the aforementioned components, FIG. 4 illustrates a cost accounting method in accordance with embodiments of the invention. The method begins in step 400. The system performs bill processing in step 412 and general ledger maintenance in step 414, while contemporaneously performing automated capture in step 402 and information retrieval in step 404. The bill processing and general ledger maintenance steps may be performed through the central information system 100, cost accounting system 200, or other component configured for receiving bills from pharmaceutical companies, equipment distributors, etc., entering the bills into a computer system, and adding the bills to a computerized general ledger.

The automated capture step 402 may be performed with the information capture device 10 as described above. As set forth above, the information capture device 10 preferably includes a scanner or other mechanism for reading identifiers such as barcodes or RFIDs associated with a caregiver, a patient, a medication, or a piece of equipment. The information capture device 10 may capture each dispensation of medication, each use of equipment, and each procedure performed on a patient or performed by a caregiver. By using the clinical information 310 including the EHR, each clinical attribute pertaining to a patient's stay is captured in the system. This includes, but is not limited to results, timing of an activity, resource time spent on an activity, medication administration timing etc. As these clinical attributes are captured as clinical documentation and stored in the EHR, key clinical attributes are selected by the cost accountants or the cost accounting system 200. The cost accounting system 200 automatically assigns the appropriate cost allocations. By using clinical attributes as volume indicators, the cost allocation is seamless to the care processes, creating a maintained and updated cost accounting system 200.

For example, as a nurse uses the EHR to perform a follow-up assessment, administer an antibiotic or to confirm that lab work is complete, the information capture device 10 records the activity that drives the cost allocation process and stores it in the EHR, creating a well-maintained and accurate cost allocation methodology.

The cost accounting system 200 may retrieve the information, or content that includes attributes, directly from the information capture device 10 using the retrieval component 260 or from the central database 300 after the information capture device 10 has transferred the information to the central information system 100.

In step 406, the cost accounting system 200 implements the association component 270 to perform an association process. The association process includes selecting captured attributes as volume indicators. Volume indicators are a unit of measure for cost allocation. The association component 270 selects volume indicators from the captured content. In order to produce the most accurate concept of a cost, the volume indicator may desirably be at the lowest common denominator. By allocating costs to items of finer granularity that form the procedure, the cost accountant, through the cost accounting system 200, can more clearly understand the costs being used for that procedure and ultimately have better control over these costs. For instance, the association component 406 may receive all descriptive attribute costs or receive the information to determine descriptive attribute costs and combine the descriptive attribute costs for a selected patient. Thus, the retrieval component 260 may retrieve information from the general ledger 330 and captured content from the information capture device 10. Many pieces of captured content can be associated with a selected patient and combined to allocate all costs for all content associated with the patient. The association component 270 may develop costs at the clinical event level, the charge level, the activity level, the clinical encounter level, or at other selected levels. Regardless of which level is selected, the association component 270 may begin with a fine level of granularity characterized by the descriptive attribute. After determining the appropriate volume indicator, the system proceeds to step 408 for implementation.

In step 408, the cost accounting system 200 uses the implementation component 280 to perform an implementation process. The implementation component 280 may allocate general ledger costs to cost centers based upon the association of clinical attributes with cost center activities. The implementation component 280 may assign costs to an organizational unit or department based upon the association made at the finer granular level. In order to achieve these goals, the implementation component 280 may include appropriate cost algorithms and may include additional cost algorithms to further roll up costs by population. For instance, the implementation component 280 may roll up costs by product lines, services, physician, payer, or programs. Furthermore, the implementation component 280 can produce summarized cost information along virtually any dimension of the patient population. The implementation component 280 may produce cost analyses by physician, surgeon, procedure, and case. The implementation component 280 may also be configured to produce cost analyses by service line, diagnoses, program, department, financial class, payer, insurance plan, and contract.

In operation, some traditional approaches would allocate a cost to the procedure of a chest x-ray. However, several clinical attributes make up this procedure. For the postero-anterior view, the radiology technician typically positions the shield, prepares the patient, provides instructions, activates the radiographic equipment, and removes the exposed film and replaces it with new, unexposed film. The technician repeats all of these steps for a lateral view. Each step in the process is an attribute. Any of these detailed steps could have a larger impact to the total cost of the procedure. To truly find the most cost effective technique for performing a chest x-ray, the cost accounting system 200 analyzes costs by and allocates costs to each clinical attribute.

Allocating costs using the lowest common denominator, the clinical or descriptive attribute, supports the ability to analyze the costliness of detailed activities that would not be supported by procedure level allocations. For instance, the disclosed system may support incorporating the cost of registered nurse time to take vital signs or the cost for each hour a patient is on a ventilator. By analyzing clinical details, the cost accounting system 200 can reveal detailed costs instead of average procedure costs applied to a broader procedure definition.

An additional example is illustrated with reference to a total knee procedure. Using an embodiment of the invention, costs may be allocated to the discrete steps that form the total knee procedure, and the steps captured as part of the clinical documentation of the care provided. Total knee procedure steps can be grouped into the classifications of pre-operative and circulating, each of which has detailed steps. For example, the pre-operative steps would include reviewing the surgery plan, performing a follow-up assessment, administering antibiotics, confirming that lab work is complete, confirming the arrival of implants and supplies, and shaving the patient. The circulating steps could include documenting intra-operative events, assisting the surgical team, monitoring and assessing the patient, obtaining add-on items as needed, administering and documenting blood information, communicating a report to a recovery area, and transporting the patient to the recovery area. The clinical details give the cost accountant, through the cost accounting system 200, insight into which detailed step (or attribute) is having the largest impact to the overall costliness of the procedure, ultimately improving the accuracy of the cost accounting results.

The process of using descriptive attributes and events as volume indicators for the cost allocation process will bring benefits to the users of this process that have been absent in traditional cost accounting processes in healthcare. One benefit includes automated association and accumulation of volumes, which provides simplified methodology for maintaining and generating cost accounting results. Another benefit includes improved accuracy of cost accounting results through use of increased granularity of healthcare volume indicators.

While particular embodiments of the invention have been illustrated and described in detail herein, it should be understood that various changes and modifications might be made to the invention without departing from the scope and intent of the invention. The embodiments described herein are intended in all respects to be illustrative rather than restrictive. Alternate embodiments will become apparent to those skilled in the art to which the present invention pertains without departing from its scope.

From the foregoing it will be seen that this invention is one well adapted to attain all the ends and objects set for above, together with other advantages, which are obvious and inherent to the system and method. It will be understood that certain features and sub-combinations are of utility and may be employed without reference to other features and sub-combinations. This is contemplated and within the scope of the appended claims.

What is claimed is:

1. One or more computer-storage media having computer-executable instructions embodied thereon that, when executed, cause a computing device to perform a method for generating cost accounting information in a healthcare environment, the method comprising:
    capturing, in an electronic health record, information associated with a patient, wherein the information associated with the patient includes an identification of the patient, an identification of a caregiver, and a healthcare procedure to perform for the patient;
    automatically retrieving, at the computing device, the information including a plurality of discrete steps that are performed during the healthcare procedure and are not supported by procedure level allocations, wherein at least one of the discrete steps represents a medical device associated with the patient or the healthcare procedure, and at least one of the discrete steps represents resource time for the healthcare procedure; and
    associating, at the computing device, each discrete step of the healthcare procedure that is not supported by procedure level allocations with an individual cost.

2. The computer-storage media of claim 1, further comprising combining the cost of each discrete step classified in a category in order to determine a category cost.

3. The computer-storage media of claim 2, further comprising selecting one of a procedure and an order as a category definition.

4. The computer-storage media of claim 2, further comprising selecting the patient as a category definition.

5. The computer-storage media of claim 1, wherein automatically retrieving the information including the plurality of discrete steps descriptive attributes comprises automatically retrieving the information from the electronic health record.

6. The computer-storage media of claim 1, wherein automatically retrieving the information including the discrete steps comprises automatically retrieving information pertaining to labor costs associated with the caregiver.

7. The computer-storage media of claim 1, wherein automatically retrieving the information including the plurality of discrete steps comprises automatically retrieving a record of medical device usage.

8. The computer-storage media of claim 1, further comprising storing clinical data, general ledger data and resource utilization data in a single database.

9. The computer-storage media of claim 8, wherein automatically retrieving the information including the plurality of discrete steps comprises automatically retrieving the information including the plurality of discrete steps from the single database.

10. The computer-storage media of claim 2, further comprising summarizing cost information along a patient dimension.

11. The computer-storage media of claim 10, further comprising defining the patient dimension as one of treating physician, department, diagnosis, procedure, and insurance plan.

12. A computer system for generating cost accounting information in a healthcare environment including automated information capture equipment, the system comprising:
    an information capture device for automatically capturing, in an electronic health record, information associated with a patient, wherein the information associated with the patient includes an identification of the patient, an identification of a caregiver, and a healthcare procedure to perform for the patient;
    a central information system for verifying the information captured by the information capture device; and
    a cost accounting system comprising:
        a retrieval component for retrieving the information captured by the information capture device including a plurality of discrete steps that are not supported by procedure level allocations, wherein at least one of the discrete steps represents a step that is performed during the healthcare procedure, at least one of the discrete steps represents a medical device associated with the patient or the healthcare procedure, and at least one of the discrete steps represent resource time for the healthcare procedure;
        an association component for associating each of the discrete steps of the healthcare procedure that are not supported by procedure level allocations with an individual cost, as well as associating each of the medical device and the resource time for the healthcare procedure with respective individual costs; and
        an implementation component for generating cost accounting information based on created associations, wherein the cost accounting information includes costs associated with each of the discrete steps of the healthcare procedure that are not supported by procedure level allocations.

13. The system of claim 12, further comprising a central database for storing captured data, the captured data including clinical data, resource utilization data, and general ledger data.

14. The system of claim 13, wherein the retrieval component retrieves captured data from the central database.

15. The system of claim 13, wherein the stored clinical data comprises electronic health records.

16. The system of claim 13, wherein the resource utilization data comprises resource time spent on an activity.

17. The system of claim 13, wherein the association component includes cost algorithms for calculating costs at a selected granularity level.

18. The system of claim 17, wherein the granularity level comprises a procedure level, the procedure level composed of descriptive attributes.

19. The system of claim 17, wherein the selected level of granularity comprises a patient level, the patient level composed of descriptive attributes.

20. The system of claim 12, wherein the implementation component comprises cost algorithms for summarizing costs by population.

21. The system of claim 12, wherein the implementation component comprises cost algorithms for producing an analysis by one of physician, surgeon, procedure, case, and insurance plan.

* * * * *